(12) United States Patent
Miura et al.

(10) Patent No.: US 6,428,795 B2
(45) Date of Patent: *Aug. 6, 2002

(54) SKIN TREATMENT COMPOSITION

(76) Inventors: Yoshimasa Miura; Sadaki Takata; Kazuo Takahashi, all of c/o Shiseido Research Center (1), 1050, Nippa-cho, Koboku-ku, Yokohama-shi, Kanagawa 223 8553 (JP); Fukuji Suzuki, 48-19, Matsukagedai, Atsugi-shi, Kanagawa 243-0207 (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/365,235

(22) Filed: Jul. 30, 1999

(30) Foreign Application Priority Data

Jul. 31, 1998 (JP) .......................... 10-229972

(51) Int. Cl.⁷ .................. A61K 6/00; A61K 7/42; A61K 7/38; A61K 7/06
(52) U.S. Cl. .................. 424/401; 424/59; 424/69; 424/68; 424/70
(58) Field of Search .................. 424/401, 59, 68

(56) References Cited

U.S. PATENT DOCUMENTS

| 5,015,469 A | * | 5/1991 | Yoneyama et al. | .......... 424/59 |
|---|---|---|---|---|
| 5,628,989 A | | 5/1997 | Harashima et al. | |
| 5,763,497 A | * | 6/1998 | Ikeda et al. | .......... 514/943 |
| 5,928,660 A | * | 7/1999 | Kobayashi et al. | .......... 424/401 |
| 5,945,471 A | * | 8/1999 | Morita et al. | .......... 524/409 |

FOREIGN PATENT DOCUMENTS

| EP | 0295886 A2 | 12/1988 |
|---|---|---|
| EP | 0393511 A2 | 10/1990 |
| EP | 0590192 A1 | 4/1994 |
| EP | 0722972 A1 | 7/1996 |
| EP | 0827983 A2 | 3/1998 |
| EP | 0829253 A2 | 3/1998 |

OTHER PUBLICATIONS

Patent Abstracts of Japan, vol. 1998, No. 04, Mar. 31, 1998 & JP 09 316492 A, Dec. 9, 1997.

Patent Abstracts of Japan, vol. 1998, No. 13, Nov. 30, 1998 & JP 10 203932A, Aug. 4, 1998.

* cited by examiner

Primary Examiner—Thurman K. Page
Assistant Examiner—Isis Ghali

(57) ABSTRACT

The invention provides an external-use composition imparting no sticky sensation in use, particularly an external-use composition for a cosmetic composition exhibiting excellent retention during use, by finding a gelling agent for an oily ingredient, particularly for silicone oil. The external-use composition contains a spherical powder (mean particle size: 0.1–200 μm) of organopolysiloxane elastomer having a JIS A hardness of 1.0–30.

6 Claims, No Drawings

SKIN TREATMENT COMPOSITION

BACKGROUND OF THE INVENTION

1. Field of the Invention

The present invention relates to a composition for external use (hereinafter referred to as an external-use composition), and more particularly, to an external-use composition useful as a cosmetic composition.

2. Background Art

Conventionally, a spherical powder of an organopolysiloxane elastomer, having characteristic elasticity, has been developed as a powder for cosmetic compositions and has been incorporated into a variety of products. Such a powder exhibits favorable properties when incorporated into cosmetic compositions, i.e., the cosmetic composition containing such a powder exhibits good skin fittability and spreadability on the skin; imparts a light and smooth sensation when applied by rubbing; has a soft-touch sensation; and imparts no strange sensation or irritation to the skin (Japanese Patent Application Laid-Open (kokai) No. 2-243612 and Japanese Patent Publication (kokoku) Nos. 4-17162 and 4-66446).

Meanwhile, a gelling agent for an oily ingredient is used in order to thicken an oily ingredient in an external-use composition. Conventionally, gelling agents such as metallic soap, organic-compound-modified clay minerals, and oil-soluble polymers have been known to gel hydrocarbon oils and ester oils. However, hydrocarbon oils and ester oils per se are sticky and oily, and such drawbacks limit use thereof in an external-use composition, even though gelling agents therefor are available.

In contrast, silicone oils, having favorable characteristics such as a light sensation for use and an non-sticky touch to the skin, has been widely used in external-use compositions in recent years. However, few gelling agents for gelling silicone oil are known; an example of which is a certain type of polyether-modified silicone disclosed in Japanese Patent Application Laid-Open (kokai) No. 7-215817. In addition, a gel-type composition in which silicone oil is gelled by use of the polyether-modified silicone exhibits slight stickiness which is characteristic to polymers.

SUMMARY OF THE INVENTION

In view of the foregoing, an object of the present invention is to provide an external-use composition imparting no sticky sensation in use, particularly an external-use composition for cosmetic compositions exhibiting excellent retention on the skin during use (hereinafter called "cosmetic retention"), by finding a gelling agent for an oily ingredient, particularly for silicone oil.

In order to overcome the drawbacks, the present inventors have conducted earnest studies on a spherical powder of organopolysiloxane elastomer, and have found that a spherical powder of organopolysiloxane elastomer having a JIS A hardness as low as 1.0–30 has excellent oil-absorbability and serves as a gelling agent for an oily ingredient, particularly silicone oil, as compared with a conventionally used spherical powder of organopolysiloxane elastomer having a JIS A hardness of 35–80.

The inventors have also found that an external-use composition containing such a spherical powder of organopolysiloxane elastomer having excellent oil-absorbability imparts no sticky sensation in use and exhibits further improved skin fittability and spreadability on the skin; and imparts a further improved light and smooth sensation when applied by rubbing (hereinafter referred to as light and smooth application sensation), as compared with a conventionally used spherical powder of organopolysiloxane elastomer having a JIS A hardness of 35–80, and has excellent stability with the passage of time. Particularly, when the composition serves as a cosmetic composition, the cosmetic composition exhibits excellent cosmetic retention. The present invention has been accomplished based on this finding.

Accordingly, in one aspect of the present invention, there is provided an external-use composition containing a spherical powder of organopolysiloxane elastomer having a JIS A hardness of 1.0–30 that has a mean particle size of 0.1–200 μm.

Preferably, the external-use composition contains the spherical powder of organopolysiloxane elastomer in an amount of 0.1–50.0 wt. % based on the entirety of the composition.

Particularly, the external-use composition is suitable for cosmetic compositions.

As used herein, the term "mean particle size" refers to a value which is obtained by measuring the diameters in a specific direction of particles under an optical microscope and dividing the sum of respective diameters of particles by the number of measured particles.

The term "JIS A hardness" refers to a hardness measured according to JIS K 6301 by use of the JIS A hardness meter.

The present invention provides an external-use composition having excellent spreadability on the skin, good light and smooth application sensation and skin fittability, and non-sticky sensation in use. Particularly, the present invention provides a cosmetic composition having greatly improved cosmetic retention.

DETAILED DESCRIPTION OF PREFERRED EMBODIMENTS

Modes for carrying out the present invention will next be described.

The spherical powder of organopolysiloxane elastomer which is incorporated into the external-use composition of the present invention is composed of an organopolysiloxane elastomer having a JIS A hardness of 1.0–30, preferably 1.0–10. When the JIS A hardness is less than 1.0, the external-use composition containing the powder disadvantageously imparts a sticky sensation in use, whereas when the hardness is in excess of 30, gelling property of the powder is unfavorably markedly deteriorated.

The spherical powder of organopolysiloxane elastomer that is incorporated into the external-use composition of the present invention has a mean particle size of 0.1–200 μm, preferably 0.5–20.0. When the particle size is less than 0.1 μm, a smooth application sensation disadvantageously disappears, whereas when the particle size is in excess of 200 μm, the powder causes an unfavorable rough sensation when applied by rubbing.

The spherical powder of organopolysiloxane elastomer which is incorporated into the external-use composition of the present invention may be a perfectly spherical powder or an oblate spherical powder. However, a perfect spherical powder is more preferable in that the composition containing the powder imparts a more favorable smoother application sensation.

No particular limitation is imposed on the method for producing the spherical powder (having a mean particle size of 0.1–200 μm) of organopolysiloxane elastomer having a JIS A hardness of 1.0–30, and the powder can generally be produced by use of a curable organopolysiloxane composition as a raw material. Examples of the curable organopolysiloxane composition include:

an addition-curable organopolysiloxane composition which is cured through addition reaction between a diorganopolysiloxane having a silicon-bonded hydrogen atom and an organopolysiloxane having a silicon-bonded lower alkenyl group such as a vinyl group conducted in the presence of a platinum catalyst;

a condensation-curable organopolysiloxane composition which is cured through dehyrogenation reaction between a diorganopolysiloxane having hydroxyl groups at both molecule ends and a diorganopolysiloxane having a silicon-bonded hydrogen atom conducted in the presence of an organotin compound;

a condensation-curable organopolysiloxane composition which is cured through condensation reaction, such as dehydration or removal of alcohol, oxime, amine, amide, carboxylic acid, ketone, etc., between a diorganopolysiloxane having hydroxyl groups at both molecule ends and hydrolyzable organosilanes conducted in the presence of an organotin compound or titanate;

a peroxide-curable organopolysiloxane composition which is cured by the application of heat in the presence of an organic peroxide catalyst; and a high-energy-ray-curable organopolysiloxane composition which is cured through radiation of γ-rays, UV-rays, or an electron beam.

Among these curable organopolysiloxane compositions, an addition-curable organopolysiloxane composition is preferred, in view of a high curing rate and homogeneity in curing. A particularly preferable composition comprises (A) a diorganopolysiloxane having at least two silicon-bonded hydrogen atoms in the molecule; (B) an organopolysiloxane having at least two lower alkenyl groups in the molecule; and (C) a platinum catalyst.

An organic group other than a lower alkenyl group may also bond to a silicon atom in an organopolysiloxane or a diorganopolysiloxane serving as a predominant component of the above-mentioned curable organopolysiloxane composition, and examples of such an organic group include an alkyl group such as methyl, ethyl, propyl, butyl, or octyl; a substituted alkyl group such as 2-phenylethyl, 2-phenylpropyl, 3,3,3-trifluoropropyl; an aryl group such as phenyl, tolyl, or xylyl; and a monovalent hydrocarbyl group having a substituent such as an epoxy, carboxylate, or mercapto group.

Several methods may be employed for producing the spherical powder (having a mean particle size of 0.1–200 μm) of organopolysiloxane elastomer having a JIS A hardness of 1.0–30 from the above-mentioned curable organopolysiloxane composition. Examples of the methods include the following (1) to (4):

(1) a method which involves mixing an addition-curable, condensation-curable, or peroxide-curable organopolysiloxane composition with water in the presence of a surfactant such as a nonionic, anionic, cationic, or amphoteric surfactant; forming a homogeneous aqueous dispersion by use of an apparatus such as a homogenization mixer, a colloid mill, a homogenizer, or a propeller mixer; releasing the dispersion into hot water at 50° C. or higher to thereby perform curing; and drying, (2) a method which involves spraying an addition-curable, condensation-curable, or peroxide-curable organopolysiloxane composition directly into hot air-flow to thereby perform curing, (3) a method which involves spraying a high-energy-ray-curable organopolysiloxane composition under exposure to high-energy rays to thereby perform curing, and (4) a method which involves curing an addition-curable, condensation-curable, peroxide-curable, or high-energy-ray-curable organopolysiloxane composition and crushing the cured product by use of a known crushing apparatus such as a ball mill, an atomizer, a kneader, or a roll mill.

Of these, the method (1) is preferred in that a powder having a more spherical particle shape and a small variation in particle size can be produced.

A spherical powder of organopolysiloxane elastomer is described in detail in Japanese Patent Application Laid-Open (kokai) No. 2-243612 and Japanese Patent Publication (kokoku) Nos. 4-17162 and 4-66446.

The external-use composition according to the present invention contains the above-described spherical powder of organopolysiloxane elastomer in an amount of preferably 0.1–50.0 wt. % based on the entirety of the composition, particularly preferably 1.0–20.0 wt. %. When the content is less than 0.1 wt. %, an intended effect on improvement in use-related characteristics provided by the present invention, such as imparting no sticky sensation in use and a light and smooth application sensation, is poor, whereas when the content is in excess of 50.0 wt. %, the resultant external-use composition disadvantageously exhibits sluggish spreadability on the skin and imparts a rough sensation.

In addition to the above-described spherical powder of organopolysiloxane elastomer, a pigment powder may be incorporated into the external-use composition according to the present invention. No particular limitation is imposed on the pigment powder so long as it is one that is typically incorporated into an external-use composition, and any pigment powder such as an inorganic pigment powder or an organic pigment powder may be incorporated.

Example of the inorganic pigments include talc, kaolin, calcium carbonate, zinc flower, titanium dioxide, red iron oxide, yellow iron oxide, black iron oxide, ultramarine, titanium-coated mica, bismuth oxychloride, a binderg pigment, ultramarine pink, hydrated chromium oxide, titanated mica, chromium oxide, cobalt aluminum oxide, iron blue, carbon black, silicic anhydride, magnesium silicate, bentonite, mica, sericite, zirconium oxide, magnesium oxide, zinc oxide, titanium oxide, precipitated calcium carbonate, heavy calcium carbonate, light magnesium carbonate, heavy magnesium carbonate, and calamine.

Examples of the organic pigments include polyester, polymethylmethacrylate, cellulose, Nylon-12, Nylon-6, styrene.acrylic acid copolymers, polypropylene, poly(vinyl chloride), nylon powder, polyethylene powder, benzoguanamine powder, tetrafluoroethylene powder, boron nitride, fish scale flake, lake tar pigments, lake natural pigments, and inorganic-organic hybrid pigments.

Preferably, the pigment powder is hydrophobicized. No particular limitation is imposed on the hydrophobicized pigment powder so long as the powder has a hydrophobic surface. Examples of such powders include a pigment powder surface-treated with high-viscosity silicone; a pigment powder coated with a silicone resin which has been preliminary reacted with alkyl hydrogen polysiloxane; silicone-coated powder further treated with alkene; a pigment powder treated with one or more surfactants selected from a cationic surfactant, an anionic surfactant, and a nonionic surfactant; a wax-coated pigment powder; a pigment powder treated with dextrinized fatty acid; and a pigment powder treated with a fluorine compound containing a perfluoroalkyl group.

The external-use composition according to the present invention contains powders including the above-described spherical powder of organopolysiloxane elastomer in an amount of 0.1–60.0 wt. % based on the entirety of the composition, particularly preferably 1.0–40.0 wt. %.

The external-use composition according to the present invention may be used as a cosmetic composition, a drug composition, a quasi-drug composition, etc. When the external-use composition according to the present invention is used as a make-up cosmetic composition such as a foundation, advantages of the present invention are particularly notable, as the above-described spherical powder of organopolysiloxane elastomer absorbs sebum to thereby provide a cosmetic composition exhibiting excellent cosmetic retention.

The form of the external-use composition according to the present invention is not particularly limited, and the composition may be used in the forms of liquid, milky-lotion, ointment, cream, gel, etc., so long as the composition is applicable to the skin.

In addition to powders including the above-described spherical powder of organopolysiloxane elastomer, one or more ingredients which are typically added to an external-use composition, such as an oily ingredient or water, may be incorporated into the external-use composition according to the present invention without impairing the effects of the present invention and in accordance with the form.

Examples of the oily ingredient which is incorporated into the external-use composition according to the present invention include:

silicone oils such as dimethylpolysiloxane, dimethylcyclopolysiloxane, methylphenyl polysiloxane, methyl hydrogen polysiloxane, higher fatty acid-modified organopolysiloxane, higher alcohol-modified organopolysiloxane, trimethylsiloxysilicate, and decamethylcyclopentanesiloxane;

hydrocarbon oils such as liquid paraffin, squalane, vaseline, polyisobutylene, and microcrystalline wax;

ester oils such as isopropyl myristate, myristyl octyldodecanol, and di(2-ethylhexyl) succinate;

glycerides such as neopentyl glycol diisooctanoate, glyceryl monostearate, triglyceryl monoisostearate, and triglyceryl cocoate;

oils and fats such as castor oil and olive oil;

lower alcohols such as ethanol;

higher alcohols such as octyldodecanol, hexadecyl alcohol, cetyl alcohol, oleyl alcohol, stearyl alcohol, and polyethylene glycol;

higher fatty acids such as lauric acid, palmitic acid, oleic acid, stearic acid, and isostearic acid;

waxes such as lanolin and beeswax; and fluorocarbon oils.

Such oily ingredients are preferably incorporated in an amount of 10.0–95.0 wt. % based on the entirety of the composition.

When the external-use composition according to the present invention is emulsified, the water content of the composition is typically 1.0–80.0 wt. % based on the entirety of the composition.

Other additives may also be incorporated into the external-use composition according to the present invention, so long as the effects of the present invention are not impaired.

Examples of such additives include humectants such as polyhydric alcohol (e.g., glycerin), mucopolysaccharides (e.g., sodium hyaluronate), and organic acids and salts thereof (e.g., amino acids, amino acid salts, and hydroxy acid salts);

surfactants such as cationic surfactants, anionic surfactants, and nonionic surfactants;

pharmaceuticals such as vitamin E and vitamin E acetate;

astringents; antioxidants; preservatives; perfume; pH regulators such as sodium secondary phosphate; clay minerals; thickeners; and ultraviolet absorbents.

Of these, a humectant is preferably incorporated into the composition in order to prevent evaporation of water from the external-use composition per se.

Specific formulations of the external-use composition of the present invention are described below.

EXAMPLES

The present invention is described in more detail by way of examples, which should not be construed as limiting the invention thereto.

Throughout the examples, unless otherwise stated, the amount of an incorporated ingredient represents weight % with respect to the entirety of the composition containing the ingredient.

JIS A hardness of an organopolysiloxane elastomer and the mean particle size of a spherical powder of organopolysiloxane elastomer were measured by the following methods. In addition, a sensory test of the cosmetic composition containing the powder was performed as described below.

<JIS A Hardness of Organopolysiloxane Elastomer>

An organopolysiloxane composition serving as a raw material was heated in a convection oven at 150° C. for one hour, to thereby prepare an organopolysiloxane elastomer. After the elastomer was cooled to room temperature, JIS A hardness of the elastomer was measured by use of a JIS A hardness meter specified by JIS K 6301.

<Mean Particle Size of Spherical Powder of Organopolysiloxane Elastomer>

Particles were observed under an optical microscope in order to measure the sizes thereof, and a mean value was calculated.

<Sensory Test>

A sensory test of the cosmetic composition was performed by a panel of 10 cosmetic experts in terms of the following five items: (1) spreadability, (2) light application sensation, (3) skin fittablility, (4) non-stickiness, and (5) cosmetic retention. Regarding each item, in the case where 8 or more panelists evaluated the item as "good," a rating AA was given; in the case where 6–7 panelists evaluated the item as "good," a rating BB was given; in the case where 4–5 panelists evaluated the item as "good," a rating CC was given; and in the case where 3 or fewer panelists evaluated the item as "good," a rating DD was given.

Cosmetic retention of the cosmetic composition was evaluated by observation of the degree of make-up deterioration after a practical test during which subjects walked for two hours. "Good cosmetic retention" refers to the case where little or no deterioration of the makeup was visually observed by the panelist and the makeup remained mostly intact on the skin.

Examples 1 to 4 and Comparative Examples 1 to 4

A gel foundation containing the following ingredients was prepared in accordance with a method as described below.

The foundation was subjected to a sensory test, and the results are shown in Table 1 along with the type of powder (6) employed. In Comparative Example 1, silicone-treated talc was incorporated in an amount of 8.0 wt. % in place of powder (6).

A method for producing the spherical powders of organopolysiloxane elastomer (A to F) shown in Table 1 is described later. Polymethylsilsesquioxane powder G is commercially available Tospearl (product of Toshiba Silicone Co., Ltd.). Each powder was subjected to measurement of JIS A hardness, mean particle size, oil absorption with respect to decamethylcyclopentasiloxane, and viscosity when dispersed in decamethylcyclopentasiloxane. Results are shown in Table 2.

| Ingredient | Amount (wt. %) |
|---|---|
| (1) silicone-treated talc | 10.0 |
| (2) silicone-treated sericite | 3.0 |
| (3) silicone-treated mica | 3.0 |
| (4) silicone-treated titanium dioxide | 6.0 |
| (5) silicone-treated color pigment | 3.0 |
| (6) powder | 8.0 |
| (7) decamethylcyclopentasiloxane | 50.0 |
| (8) polyether-modified silicone | 4.0 |
| (9) diglyceryl diisostearate | 1.0 |
| (10) ethyl alcohol | 6.0 |
| (11) purified water | 6.0 |

<Method of Production>

Ingredient (6) was dispersed in ingredient (7), and powders of ingredients (1) to (5) were further dispersed in the resultant dispersion. Subsequently, ingredients (8) and (9) were dissolved into the resultant dispersion, to thereby obtain an oil phase. An aqueous phase, a mixture of ingredients (10) and (11), was added to the oil phase with stirring. The resultant mixture was deaerated and charged into a container, to thereby obtain a gel foundation.

As is apparent from Table 1, foundations containing a spherical powder of organopolysiloxane elastomer having a JIS A hardness of more than 30 exhibit rating "CC" with respect to all evaluation items (1) to (5) in the above-described sensory test. As is also apparent from Table 1, foundations containing a spherical powder of organopolysiloxane elastomer having a JIS A hardness of 1.0–30 exhibit rating "AA" or "BB" with respect to all evaluation items (1) to (5) in the above-described sensory test. Thus, these foundations were confirmed to have excellent properties in terms of skin fittatibility, light application sensation, spreadability, non-stickiness, and cosmetic retention.

Method for Producing Spherical Powder of Organopolysiloxane Elastomer (Powder A)

Polydimethylsiloxane having dimethylvinylsiloxy groups at both ends of the molecular chain (vinyl equivalent=5000) (100 parts by weight), dimethylsiloxane.methylhydrogensiloxane copolymer having trimethylsiloxy groups at both ends of the molecular chain (4.5 parts by weight), dimethylpolysiloxane having trimethylsiloxy groups at both ends of the molecular chain (viscosity: 100 cSt) (50 parts by weight), and an isopropanol solution containing platinic chloride (an amount as reduced to 50 ppm of platinum with respect to the entirety of the resultant composition) were homogeneously blended at 5° C., to thereby prepare a liquid organopolysiloxane composition.

This liquid organopolysiloxane composition was quickly mixed into an aqueous solution (300 parts by weight) containing pure water (electric conductivity: 0.2 µS/cm) and 2 wt. % of polyoxyethylene (9 mol-added) lauryl ether at 25° C. Subsequently, the resultant mixture was treated by use of a homogenizer (300 kgf/cm$^2$), to thereby prepare an aqueous dispersion in which a liquid organopolysiloxane composition was homogeneously dispersed.

The resultant aqueous dispersion was allowed to stand at 30° C. for 6 hours, and then heated at 80° C. for 1 hour, to thereby cure the composition. Subsequently, the aqueous dispersion was dried by use of a spray dryer, to thereby obtain a spherical powder of organopolysiloxane elastomer (powder A).

TABLE 1

|  | Example | | | | Comparative Example | | | |
|---|---|---|---|---|---|---|---|---|
|  | 1 | 2 | 3 | 4 | 1 | 2 | 3 | 4 |
| Powder used as ingredient (6) | A | B | C | D | None | E | F | G |
| Sensory test | | | | | | | | |
| (1) Spreadability | AA | AA | AA | BB | DD | CC | CC | DD |
| (2) Light application sensation | AA | BB | BB | BB | DD | CC | CC | DD |
| (3) Skin fittability | AA | BB | BB | BB | DD | CC | CC | DD |
| (4) Non-stickiness | AA | AA | AA | BB | CC | CC | CC | DD |
| (5) Cosmetic retention | AA | AA | AA | BB | DD | CC | CC | DD |
| State of composition | gel | Gel | Gel | gel | liquid | gel | gel | gel |
| Hardness of composition (30° C.)*1 | 24 | 18 | 12 | 8 | not measurable | 6 | 5 | 1 |

*1 Hardness was measured by use of a curd tension meter with a load of 200 g and a pressure-sensitive shaft of 8φ.

Method for Producing Spherical Powder of Organopolysiloxane Elastomer (Powder B)

Polydimethylsiloxane having dimethylvinylsiloxy groups at both ends of the molecular chain (vinyl equivalent=5000) (100 parts by weight), dimethylsiloxane-methylhydrogensiloxane copolymer having trimethylsiloxy groups at both ends of the molecular chain (4.5 parts by weight), dimethylpolysiloxane having trimethylsiloxy groups at both ends of the molecular chain (viscosity: 100 cSt) (50 parts by weight), and an isopropanol solution containing platinic chloride (an amount as reduced to 50 ppm of platinum with respect to the entirety of the resultant composition) were homogeneously blended at 5° C., to thereby prepare a liquid organopolysiloxane composition.

This liquid organopolysiloxane composition was quickly mixed into an aqueous solution (300 parts by weight) containing pure water (electric conductivity: $0.2\,\mu$S/cm) and 2 wt. % of polyoxyethylene (9 mol-added) lauryl ether at 25° C. Subsequently, the resultant mixture was treated by use of a homogenizer (200 kgf/cm$^2$), to thereby prepare an aqueous dispersion in which a liquid organopolysiloxane composition was homogeneously dispered.

The resultant aqueous dispersion was allowed to stand at 30° C. for 6 hours, and then was heated at 80° C. for 1 hour, to thereby cure the composition. Subsequently, the aqueous dispersion was dried by use of a spray dryer, to thereby obtain a spherical powder of organopolysiloxane elastomer (powder B).

Method for Producing Spherical Powder of Organopolysiloxane Elastomer (Powder C)

Polydimethylsiloxane having dimethylvinylsiloxy groups at both ends of the molecular chain (vinyl equivalent=2500) (100 parts by weight), polymethylhydrogensiloxane having trimethylsiloxy groups at both ends of the molecular chain (viscosity: 20 mPa·s) (5.2 parts by weight), and an isopropanol solution containing platinic chloride (an amount as reduced to 50 ppm of platinum with respect to the entirety of the resultant composition) were homogeneously blended at 5° C., to thereby prepare a liquid organopolysiloxane composition.

This liquid organopolysiloxane composition was heated in a convection oven at 150° C. for one hour, to thereby cure the composition and obtain an organopolysiloxane elastomer. Subsequently, the organopolysiloxane elastomer was pulverized by use of a pulverizer for 3 hours, and passed through a 100-mesh sieve, to thereby to obtain a spherical powder of organopolysiloxane elastomer (powder C).

Method for Producing Spherical Powder of Organopolysiloxane Elastomer (Powder D)

Polydimethylsiloxane having dimethylvinylsiloxy groups at both ends of the molecular chain (vinyl equivalent=5000) (100 parts by weight), dimethylsiloxane.methylhydrogensiloxane copolymer having trimethylsiloxy groups at both ends of the molecular chain (4.5 parts by weight), and an isopropanol solution containing platinic chloride (an amount as reduced to 50 ppm of platinum with respect to the entirety of the resultant composition) were homogeneously blended at 5° C., to thereby prepare a liquid organopolysiloxane composition.

This liquid organopolysiloxane composition was quickly mixed into an aqueous solution (300 parts by weight) containing pure water (electric conductivity: $0.2\,\mu$S/cm) and 2 wt. % of polyoxyethylene (9 mol-added) lauryl ether at 25° C. Subsequently, the resultant mixture was treated by use of a homogenizer (300 kgf/cm$^2$), to thereby prepare an aqueous dispersion in which a liquid organopolysiloxane composition was homogeneously dispered.

The resultant aqueous dispersion was allowed to stand at 30° C. for 6 hours, and then heated at 80° C. for 1 hour, to thereby cure the composition. Subsequently, the aqueous dispersion was dried by use of a spray dryer, to thereby obtain a spherical powder of organopolysiloxane elastomer (powder D).

Method for Producing Spherical Powder of Organopolysiloxane Elastomer (Powder E)

Polydimethylsiloxane having dimethylvinylsiloxy groups at both ends of the molecular chain (vinyl equivalent=2500) (100 parts by weight), polymethylhydrogensiloxane having trimethylsiloxy groups at both ends of the molecular chain (viscosity: 20 mPa·s) (5.2 parts by weight), and an isopropanol solution containing platinic chloride (an amount as reduced to 50 ppm of platinum with respect to the entirety of the resultant composition) were homogeneously blended at 5° C., to thereby prepare a liquid organopolysiloxane composition.

This liquid organopolysiloxane composition was quickly mixed into an aqueous solution (300 parts by weight) containing pure water (electric conductivity: $0.2\,\mu$S/cm) and 2 wt. % of polyoxyethylene (9 mol-added) lauryl ether at 25° C. Subsequently, the resultant mixture was treated by use of a homogenizer (300 kgf/cm$^2$), to thereby prepare an aqueous dispersion in which a liquid organopolysiloxane composition was homogeneously dispered.

The resultant aqueous dispersion was allowed to stand at 30° C. for 6 hours, and then heated at 80° C. for 1 hour, to thereby cure the composition. Subsequently, the aqueous dispersion was dried by use of a spray dryer, to thereby obtain a spherical powder of organopolysiloxane elastomer (powder E).

Method for Producing Spherical Powder of Organopolysiloxane Elastomer (Powder F)

Polydimethylsiloxane having dimethylvinylsiloxy groups at both ends of the molecular chain (vinyl equivalent=2500) (100 parts by weight), polymethylhydrogensiloxane having trimethylsiloxy groups at both ends of the molecular chain (viscosity: 20 mPa·s) (5.2 parts by weight), and an isopropanol solution containing platinic chloride (an amount as reduced to 50 ppm of platinum with respect to the entirety of the resultant composition) were homogeneously blended at 5° C., to thereby prepare a liquid organopolysiloxane composition.

This liquid organopolysiloxane composition was quickly mixed into an aqueous solution (300 parts by weight) containing pure water (electric conductivity: $0.2\,\mu$S/cm) and 2 wt. % of polyoxyethylene (9 mol-added) lauryl ether at 25° C. Subsequently, the resultant mixture was treated by use of a homogenizer (200 kgf/cm$^2$), to thereby prepare an aqueous dispersion in which a liquid organopolysiloxane composition was homogeneously dispered.

The resultant aqueous dispersion was allowed to stand at 30° C. for 6 hours, and then heated at 80° C. for 1 hour, to thereby cure the composition. Subsequently, the aqueous dispersion was dried by use of a spray dryer, to thereby obtain a spherical powder of organopolysiloxane elastomer (powder F).

TABLE 2

| Powder | A | B | C | D | E | F | G |
|---|---|---|---|---|---|---|---|
| Mean particle size ($\mu$m) | 1 | 10 | 50 | 4 | 1 | 10 | 3 |

TABLE 2-continued

| Powder | A | B | C | D | E | F | G |
|---|---|---|---|---|---|---|---|
| JIS A hardness | 7 | 7 | 7 | 30 | 50 | 50 | ≧90 |
| Oil absorption with respect to decametylcyclopentasiloxane (g/100 g) | 450 | 408 | 382 | 365 | 200 | 150 | 48 |
| Viscosity at 30° C. (mPa · s)*² | 200 | 163 | 120 | 45 | 20 | 15 | 5 |

*²Viscosity was measured by dispersing a powder (10 wt. %) in decamethylcyclopentasiloxane (90 wt. %) by use of a dispersion mixer and measuring the viscosity of the resultant dispersion by use of a B-type viscometer.

As is apparent from Table 2, oil absorption of a spherical powder of organopolysiloxane elastomer increases with a reduction of JIS A hardness and with a reduction of the mean particle size.

As is apparent from Tables 1 and 2, a foundation has high hardness when it contains a spherical powder of organopolysiloxane elastomer having high oil absorption, and also, a spherical powder of organopolysiloxane elastomer having higher oil absorption has more excellent property of gelling an oily ingredient.

Further examples of the external-use composition of the present invention—Examples 5 to 14 and Comparative Examples 5 to 15—are described below. Each external-use composition was subjected to the above-described sensory test (items (1)–(5)). The results are shown in Table 3, along with the results of the sensory test in Example 1.

Example 5

Emollient Cream

| Ingredient | Amount (wt. %) |
|---|---|
| (1) ion-exchange water | balance |
| (2) glycerin | 10.0 |
| (3) methylparaben | 0.2 |
| (4) squalane | 20.0 |
| (5) cetyl octanoate | 8.5 |
| (6) microcrystalline wax | 1.0 |
| (7) polyoxyethylene glyceryl triisostearate | 0.2 |
| (8) perfume | suitable amount |
| (9) organic compound-modified clay mineral | 1.3 |
| (10) spherical powder of organopolysiloxane elastomer (powder A) | 10.0 |

<Method of Production>

Ingredients (3) to (9) were mixed and dissolved while being heated to 70° C., to thereby prepare an oil phase, and ingredient (10) was homogeneously dispersed in the oil phase. Ingredient (2) was added to ingredient (1), and the resultant mixture was heated to 70° C. to thereby prepare an aqueous phase. The aqueous phase was added to the oil phase containing ingredient (10) in a dispersed state, with sufficient stirring. The resultant mixture was homogenized by use of a homogenization mixer and cooled to 30° C. to thereby obtain an emollient cream.

Example 6

Milky lotion

| Ingredient | Amount (wt. %) |
|---|---|
| (1) ion-exchange water | balance |
| (2) 1,3-butylene glycol | 5.0 |
| (3) liquid paraffin | 20.0 |
| (4) squalane | 10.0 |
| (5) beeswax | 2.0 |
| (6) sorbitan sesquioleate | 4.0 |
| (7) POE (20) sorbitan monooleate | 1.0 |
| (8) perfume | suitable amount |
| (9) spherical powder of organopolysiloxane elastomer (powder A) | 0.1 |

<Method of Production>

Ingredients (1) and (2) were mixed and heated to 70° C. to thereby prepare an aqueous phase. Subsequently, ingredients (3) to (8) were mixed while being heated to 70° C. Ingredient (9) was dispersed in the mixture, and the aqueous phase was slowly added to the resultant mixture, to carry out preliminary emulsification. The resultant mixture was homogenized by use of a homogenization mixer, followed by deaeration, filtration, and cooling, to thereby obtain a milky lotion.

Example 7

Water-in-oil emulsion-type foundation

| Ingredient | Amount (wt. %) |
|---|---|
| (1) ion-exchange water | balance |
| (2) 1,3-butylene glycol | 3.0 |
| (3) dimethylpolysiloxane (viscosity at 25° C.: 6 mPa · s) | 15.0 |
| (4) methylparaben | 0.1 |
| (5) polyoxyalkylene-modified organopolysiloxane | 5.0 |
| (6) decamethylcyclopentasiloxane | 20.0 |
| (7) perfume | suitable amount |
| (8) hydropobicized (silicone-treated) powder | 20.0 |
| (9) spherical powder of organopolysiloxane elastomer (powder B) | 3.0 |

<Method of Production>

Ingredients (3) to (7) were mixed and dissolved at 40° C. to thereby prepare an oil phase. Ingredients (8) and (9) were homogeneously dispersed in the oil phase, and ingredients (1) and (2) were added to the resultant mixture with sufficient stirring. The resultant mixture was homogenized by use of a homogenization mixer, to thereby obtain a water-in-oil emulsion-type foundation.

Example 8

Water-in-oil emulsion-type solid foundation

| Ingredient | Amount (wt. %) |
| --- | --- |
| (1) ion-exchange water | balance |
| (2) glycerin | 5.0 |
| (3) methylparaben | 0.1 |
| (4) polyoxyalkylene-modified organopolysiloxane | 5.0 |
| (5) decamethylcyclopentasiloxane | 20.0 |
| (6) dimethylpolysiloxane (viscosity at 25° C.: 6 mPa · s) | 5.0 |
| (7) paraffin wax | 10.0 |
| (8) hydrophobicized (silicone-treated) powder | 30.0 |
| (9) spherical powder of organopolysiloxane elastomer (powder D) | 7.0 |

<Method of Production>

Ingredients (3) to (7) were mixed and dissolved while being heated to 80° C. to prepare an oil phase, and ingredients (8) and (9) were homogeneously dispersed in the oil phase. Ingredients (1) and (2) were mixed and heated to 80° C. to prepare an aqueous phase. Subsequently, the aqueous phase was added to the oil phase with sufficient stirring. The resultant mixture was homogenized by use of a homogenization mixer, poured into an inner dish, and cooled to 30° C., to thereby obtain a water-in-oil emulsion-type solid foundation.

Example 9

Gel-type makeup base

| Ingredient | Amount (wt. %) |
| --- | --- |
| (1) ion-exchange water | balance |
| (2) 1,3-butylene glycol | 3.0 |
| (3) methylparaben | 0.15 |
| (4) polyoxyalkylene-modified organopolysiloxane | 3.0 |
| (5) decamethylcyclopentasiloxane | 25.0 |
| (6) octyl methoxycinnamate | 5.0 |
| (7) dimethylpolysiloxane | 10.0 |
| (8) spherical powder of organopolysiloxane elastomer (powder A) | 30.0 |

<Method of Production>

Ingredients (3) to (7) were mixed and dissolved at 40° C. to obtain a solution, and ingredient (8) was homogeneously dispersed in the solution, to thereby prepare an oil phase. Ingredients (1) and (2) were added to the oil phase with sufficient stirring. The resultant mixture was homogenized by use of a homogenization mixer, deaerated, and filtered to thereby obtain a makeup base.

Example 10

Water-in-oil emulsion-type foundation

| Ingredient | Amount (wt. %) |
| --- | --- |
| (1) ion-exchange water | balance |
| (2) 95% ethyl alcohol | 15.0 |
| (3) 1,3-butylene glycol | 3.0 |
| (4) methylparaben | 0.1 |
| (5) polyoxyalkylene-modified organopolysiloxane | 5.0 |
| (6) decamethylcyclopentasiloxane | 20.0 |
| (7) perfume | suitable amount |
| (8) hydrophobicized (fluorine-treated) powder | 20.0 |
| (9) spherical powder of organopolysiloxane elastomer (powder D) | 10.0 |

<Method of Production>

Ingredients (4) to (7) were mixed and dissolved at 40° C. to prepare an oil phase. Ingredients (8) and (9) were homogeneously dispersed in the oil phase, and ingredients (1) to (3) were further added to the oil phase with sufficient stirring. The resultant mixture was homogenized by use of a homogenization mixer, to thereby obtain a water-in-oil emulsion-type foundation.

Example 11

Gel-type sunscreen

| Ingredient | Amount (wt. %) |
| --- | --- |
| (1) dimethylpolysiloxane (6 cs) | 19.8 |
| (2) octamethylcyclotetrasiloxane | 30.0 |
| (3) spherical powder of organopolysiloxane elastomer (powder B) | 12.0 |
| (4) polyether-modified silicone | 20.0 |
| (5) octyl methoxycinnamate | 8.0 |
| (6) purified water | 8.0 |
| (7) ethyl alcohol | 2.0 |
| (8) methylparaben | 0.2 |

<Method of Production>

Ingredients (1), (2), (4), and (5) were mixed with stirring, and powder of (3) was dispersed in the resultant mixture, to thereby prepare an oil phase. Ingredients (7) and (8) were dissolved in ingredient (6), to prepare an aqueous phase. The aqueous phase was added to the oil phase with stirring. After deaeration, the resultant mixture was charged into a container, to thereby obtain a gel-type sunscreen.

Example 12

Pressed powder

| Ingredient | Amount (wt. %) |
| --- | --- |
| (1) talc | balance |
| (2) sericite | 10.0 |
| (3) kaolin | 5.0 |

-continued

Pressed powder

| Ingredient | Amount (wt. %) |
|---|---|
| (4) titanium dioxide | 5.0 |
| (5) zinc myristate | 5.0 |
| (6) color pigment | 3.0 |
| (7) spherical powder of organopolysiloxane elastomer (powder A) | 10.0 |
| (8) porous spherical silica (mean particle size: 3 μm) | 5.0 |
| (9) squalane | 3.0 |
| (10) glyceryl triisooctanoate | 2.0 |
| (11) preservative | suitable amount |
| (12) perfume | suitable amount |

<Method of Production>

Ingredients (1) and (6) were sufficiently mixed by use of a blender. Ingredients (2) to (5), (7), and (8) were added to the mixture, and the resultant mixture was further mixed sufficiently. Ingredients (9) to (11) were added to the resultant mixture. After the color of the mixture was adjusted, ingredient (12) was sprayed thereto and the resultant mixture was homogenized. Subsequently, the mixture was crushed by use of a crusher, passed through a sieve, and compression-molded into an inner dish, to thereby obtain a pressed powder.

Example 13

Powdery foundation

| Ingredient | Amount (wt. %) |
|---|---|
| (1) talc | balance |
| (2) sericite | 15.0 |
| (3) mica | 20.0 |
| (4) titanium dioxide | 10.0 |
| (5) color pigment | 5.0 |
| (6) spherical powder of organopolysiloxane elastomer (powder A) | 10.0 |
| (7) porous spherical resin powder ("Microsponge," product of Dow Corning Toray Co., Ltd.; mean particle size: 7 μm) | 10.0 |
| (8) squalane | 6.0 |
| (9) dimethylpolysiloxane | 3.0 |
| (10) octyl myristate | 3.0 |
| (11) sorbitan monooleate | 1.0 |
| (12) preservative, antioxidant | suitable amount |
| (13) perfume | suitable amount |

<Method of Production>

The ingredients were mixed in the same manner as described in Example 9, to thereby obtain a powdery foundation.

Example 14

Two-way foundation

| Ingredient | Amount (wt. %) |
|---|---|
| (1) silicone-treated talc | balance |
| (2) silicone-treated sericite | 15.0 |
| (3) silicone-treated mica | 30.0 |
| (4) silicone-treated titanium dioxide | 10.0 |
| (5) silicone-treated color pigment | 5.0 |
| (6) spherical powder of organopolysiloxane elastomer (powder B) | 5.0 |
| (7) squalane | 3.0 |
| (8) solid paraffin | 1.0 |
| (9) dimethylpolysiloxane | 4.0 |
| (10) octyl methoxycinnamate | 1.0 |
| (11) preservative, antioxidant | suitable amount |
| (12) perfume | suitable amount |

<Method of Production>

The ingredients were mixed in the same manner as described in Example 9, to thereby obtain a two-way (i.e., usable with or without water) foundation.

Comparative Example 5

The procedure of Example 1 was repeated except that the spherical powder of organopolysiloxane elastomer was replaced by the same amount of ion-exchange water, to thereby obtain a gel-type foundation.

Comparative Example 6

The procedure of Example 5 was repeated except that the spherical powder of organopolysiloxane elastomer was replaced by the same amount of ion-exchange water, to thereby obtain an emollient cream.

Comparative Example 7

The procedure of Example 6 was repeated except that the spherical powder of organopolysiloxane elastomer was replaced by the same amount of ion-exchange water, to thereby obtain a milky lotion.

Comparative Example 8

The procedure of Example 7 was repeated except that the spherical powder of organopolysiloxane elastomer was replaced by the same amount of ion-exchange water, to thereby obtain a water-in-oil emulsion-type foundation.

Comparative Example 9

The procedure of Example 8 was repeated except that the spherical powder of organopolysiloxane elastomer was replaced by the same amount of ion-exchange water, to thereby obtain a water-in-oil emulsion-type solid foundation.

Comparative Example 10

The procedure of Example 9 was repeated except that the spherical powder of organopolysiloxane elastomer was replaced by the same amount of ion-exchange water, to thereby obtain a gel-type makeup base.

Comparative Example 11

The procedure of Example 10 was repeated except that the spherical powder of organopolysiloxane elastomer was replaced by the same amount of ion-exchange water, to thereby obtain a water-in-oil emulsion-type foundation.

Comparative Example 12

The procedure of Example 11 was repeated except that the spherical powder of organopolysiloxane elastomer was replaced by the same amount of ion-exchange water, to thereby obtain a gel-type sunscreen.

Comparative Example 13

The procedure of Example 12 was repeated except that the spherical powder of organopolysiloxane elastomer was replaced by the same amount of ion-exchange water, to thereby obtain a pressed powder.

Comparative Example 14

The procedure of Example 13 was repeated except that the spherical powder of organopolysiloxane elastomer was replaced by the same amount of ion-exchange water, to thereby obtain a powdery foundation.

Comparative Example 15

The procedure of Example 14 was repeated except that the spherical powder of organopolysiloxane elastomer was replaced by the same amount of ion-exchange water, to thereby obtain a two-way foundation.

TABLE 3

|  | Spread-ability | Light application sensation | Skin fittability | Non-stickiness | Cosmetic retention |
|---|---|---|---|---|---|
| Example 1 | AA | AA | AA | AA | AA |
| Example 5 | AA | BB | BB | BB | AA |
| Example 6 | AA | BB | AA | AA | BB |
| Example 7 | AA | AA | AA | AA | AA |
| Example 8 | BB | BB | AA | AA | AA |
| Example 9 | BB | BB | AA | BB | AA |
| Example 10 | AA | AA | AA | AA | AA |
| Example 11 | AA | AA | AA | AA | AA |
| Example 12 | AA | AA | AA | AA | AA |
| Example 13 | AA | AA | BB | AA | AA |
| Example 14 | AA | AA | BB | AA | AA |
| Comp. Example 5 | CC | DD | CC | CC | DD |
| Comp. Example 6 | CC | CC | CC | CC | CC |
| Comp. Example 7 | BB | CC | CC | CC | CC |
| Comp. Example 8 | BB | BB | CC | BB | DD |
| Comp. Example 9 | CC | CC | CC | CC | DD |
| Comp. Example 10 | BB | CC | CC | DD | DD |
| Comp. Example 11 | BB | CC | CC | CC | CC |
| Comp. Example 12 | CC | CC | DD | DD | CC |
| Comp. Example 13 | BB | BB | BB | BB | DD |
| Comp. Example 14 | BB | BB | BB | BB | DD |
| Comp. Example 15 | BB | BB | BB | BB | DD |

As is clear from Table 3, the external-use compositions of Example 1 and Examples 5–14 are superior to compositions of Comparative Examples 5–15 in terms of skin fittability, light application sensation, spreadability, non-stickiness, and cosmetic retention.

What is claimed is:

1. An external-use gel comprising:
    a spherical powder of organopolysiloxane elastomer having a JIS A hardness of 1.0–10 and a mean particle size of 0.1–200 μm;
    silicone-treated talc; and
    an oily ingredient,
    wherein the spherical powder of organopolysiloxane elastomer is contained in an amount of 0.1–50.0 wt. % and the oily ingredient is contained in amount of 10.0–95.0 wt. % based on the entirety of the composition.

2. The external-use gel according claim 1, wherein the oily ingredient is silicone oil.

3. The external-use gel according to claim 1, wherein the gel is a cosmetic.

4. The external-use gel according to claim 1, wherein the powder has a mean particle size of 0.5–50 μm.

5. The external-use gel according to claim 1, wherein the powder has a mean particle size of 0.5–20 μm.

6. The external-use gel according to claim 1, wherein the organopolysiloxane elastomer has a JIS A hardness of 7.

* * * * *